United States Patent
Mizobuchi (10) Patent No.: US 10,893,828 B2
(45) Date of Patent: Jan. 19, 2021

(54) DETERMINATION APPARATUS, IMAGING APPARATUS, DRIVER CONFIRMATION SYSTEM, MOVEABLE BODY, AND DETERMINATION METHOD

(71) Applicant: KYOCERA Corporation, Kyoto (JP)

(72) Inventor: Tomoki Mizobuchi, Toyota (JP)

(73) Assignee: KYOCERA Corporation, Kyoto (JP)

( * ) Notice: Subject to any disclaimer, the term of this patent is extended or adjusted under 35 U.S.C. 154(b) by 74 days.

(21) Appl. No.: 16/328,700

(22) PCT Filed: Aug. 10, 2017

(86) PCT No.: PCT/JP2017/029151
§ 371 (c)(1),
(2) Date: Feb. 26, 2019

(87) PCT Pub. No.: WO2018/043100
PCT Pub. Date: Mar. 8, 2018

(65) Prior Publication Data
US 2019/0192055 A1   Jun. 27, 2019

(30) Foreign Application Priority Data
Aug. 29, 2016   (JP) .................................. 2016-167403

(51) Int. Cl.
*G06F 21/32*   (2013.01)
*G06T 7/00*   (2017.01)
(Continued)

(52) U.S. Cl.
CPC ............ *A61B 5/1171* (2016.02); *B60R 11/02* (2013.01); *B60R 16/02* (2013.01); *B60R 25/25* (2013.01);
(Continued)

(58) Field of Classification Search
CPC ....................................................... G06F 21/32
See application file for complete search history.

(56) References Cited

U.S. PATENT DOCUMENTS

2006/0072792 A1   4/2006   Toda et al.
2006/0215884 A1   9/2006   Ota
(Continued)

FOREIGN PATENT DOCUMENTS

JP   2003-027795 A   1/2003
JP   2003-237504 A   8/2003
(Continued)

*Primary Examiner* — Joshua L Schwartz
(74) *Attorney, Agent, or Firm* — Studebaker & Brackett PC (57) ABSTRACT

A determination apparatus includes a first acquisition unit, a second acquisition unit, and a controller. The first acquisition unit acquires a facial photograph image, included in a medium holding the facial photograph image, as a first facial image. The second acquisition unit acquires a captured image obtained by capturing an image of an imaging area, in which the face of a driver is assumed to be located, at a start of driving and/or during driving. The controller extracts an image of the face of the driver as a second facial image from the captured image acquired from the second acquisition unit, compares the first facial image and the second facial image, and determines whether the driver is the person in the facial photograph image held by the medium.

16 Claims, 5 Drawing Sheets

(51) Int. Cl.
*A61B 5/1171* (2016.01)
*B60R 25/25* (2013.01)
*B60R 11/02* (2006.01)
*B60R 16/02* (2006.01)
*G08B 13/00* (2006.01)

(52) U.S. Cl.
CPC ............... *G06F 21/32* (2013.01); *G06T 7/00* (2013.01); *G06T 7/0002* (2013.01); *G08B 13/00* (2013.01)

(56) References Cited

U.S. PATENT DOCUMENTS

| | | | |
|---|---|---|---|
| 2010/0232658 A1 | 9/2010 | Omoto et al. | |
| 2016/0086021 A1* | 3/2016 | Grohman | G06K 9/00288 |
| | | | 701/36 |
| 2016/0275518 A1* | 9/2016 | Bowles | G06K 9/6215 |

FOREIGN PATENT DOCUMENTS

| | | |
|---|---|---|
| JP | 2006-099395 A | 4/2006 |
| JP | 2006-168561 A | 6/2006 |
| JP | 2006-264400 A | 10/2006 |
| JP | 2007-186144 A | 7/2007 |
| JP | 2009-059007 A | 3/2009 |
| JP | 2011-225066 A | 11/2011 |
| JP | 2016-141349 A | 8/2016 |
| WO | 2007/094988 A2 | 8/2007 |

\* cited by examiner

DETERMINATION APPARATUS, IMAGING APPARATUS, DRIVER CONFIRMATION SYSTEM, MOVEABLE BODY, AND DETERMINATION METHOD

CROSS-REFERENCE TO RELATED APPLICATION

The present application claims priority to and the benefit of Japanese Patent Application No. 2016-167403 filed Aug. 29, 2016, the entire contents of which are incorporated herein by reference.

TECHNICAL FIELD

The present disclosure relates to a determination apparatus, an imaging apparatus, a driver confirmation system, a moveable body, and a determination method.

BACKGROUND

A driver confirmation system that can unlock a vehicle door, start the engine, and the like only for a legitimate driver has been proposed for apparatuses such as vehicles. For example, see patent literature (PTL) 1.

CITATION LIST

Patent Literature

PTL 1: JP200327795A

SUMMARY

A determination apparatus according to an embodiment of the present disclosure includes a first acquisition unit, a second acquisition unit, and a controller. The first acquisition unit acquires a facial photograph image, included in a medium holding the facial photograph image, as a first facial image. The second acquisition unit acquires a captured image obtained by capturing an image of an imaging area, in which a face of a driver is assumed to be located, at the start of driving and/or during driving. The controller extracts an image of the face of the driver as a second facial image from the captured image acquired from the second acquisition unit. The controller compares the first facial image and the second facial image and determines whether the driver is the person in the facial photograph image held by the medium.

An imaging apparatus according to an embodiment of the present disclosure includes an imaging unit, a first acquisition unit, and a controller. The imaging unit captures an image of an imaging area, in which a face of a driver is assumed to be located, at the start of driving and/or during driving. The first acquisition unit acquires a facial photograph image, included in a medium holding the facial photograph image, as a first facial image. The controller extracts an image of the face of the driver as a second facial image from a captured image acquired from the imaging unit. The controller compares the first facial image and the second facial image and determines whether the driver is the person in the facial photograph image held by the medium.

A driver confirmation system according to an embodiment of the present disclosure includes a camera, a reading apparatus, and a controller. The camera captures an image of an imaging area, in which a face of a driver is assumed to be located, at the start of driving and/or during driving. The reading apparatus reads a facial photograph image as a first facial image from a medium holding the facial photograph image. The controller extracts an image of the face of the driver as a second facial image from a captured image acquired from the camera. The controller compares the first facial image and the second facial image and determines whether the driver is the person in the facial photograph image held by the medium.

A moveable body according to an embodiment of the present disclosure includes a driver confirmation system. The driver confirmation system includes a camera, a reading apparatus, and a controller. The camera captures an image of an imaging area, in which a face of a driver is assumed to be located, at the start of driving and/or during driving. The reading apparatus reads a facial photograph image as a first facial image from a medium holding the facial photograph image. The controller extracts an image of the face of the driver as a second facial image from a captured image acquired from the camera. The controller compares the first facial image and the second facial image and determines whether the driver is the person in the facial photograph image held by the medium.

A determination method according to an embodiment of the present disclosure includes acquiring a facial photograph image as a first facial image from a medium holding the facial photograph image. The determination method also includes acquiring a captured image obtained by capturing an image of an imaging area, in which a face of a driver is assumed to be located, at the start of driving and/or during driving. The determination method further includes extracting an image of the face of the driver as a second facial image from the captured image. The determination method includes comparing the first facial image and the second facial image and determining whether the driver is the person in the facial photograph image held by the medium.

DETAILED DESCRIPTION

An example driver confirmation system for suspending use of a vehicle other than by a legitimate user stores an image of the driver's license of the legitimate driver in a storage apparatus. At the time of driving, the driver confirmation system compares an image of a driver's license in the driver's possession with the image of the driver's license stored in the storage means and permits the user to operate the vehicle when the image of the driver's license in the driver's possession matches the registered image of the driver's license. In contrast with this example, embodiments of the present disclosure are described below.

Embodiments of the present disclosure are described below with reference to the drawings. The drawings referred to below are schematic illustrations. The dimensional ratios and the like in the drawings do not necessarily match the actual dimensions.

Figure 1:
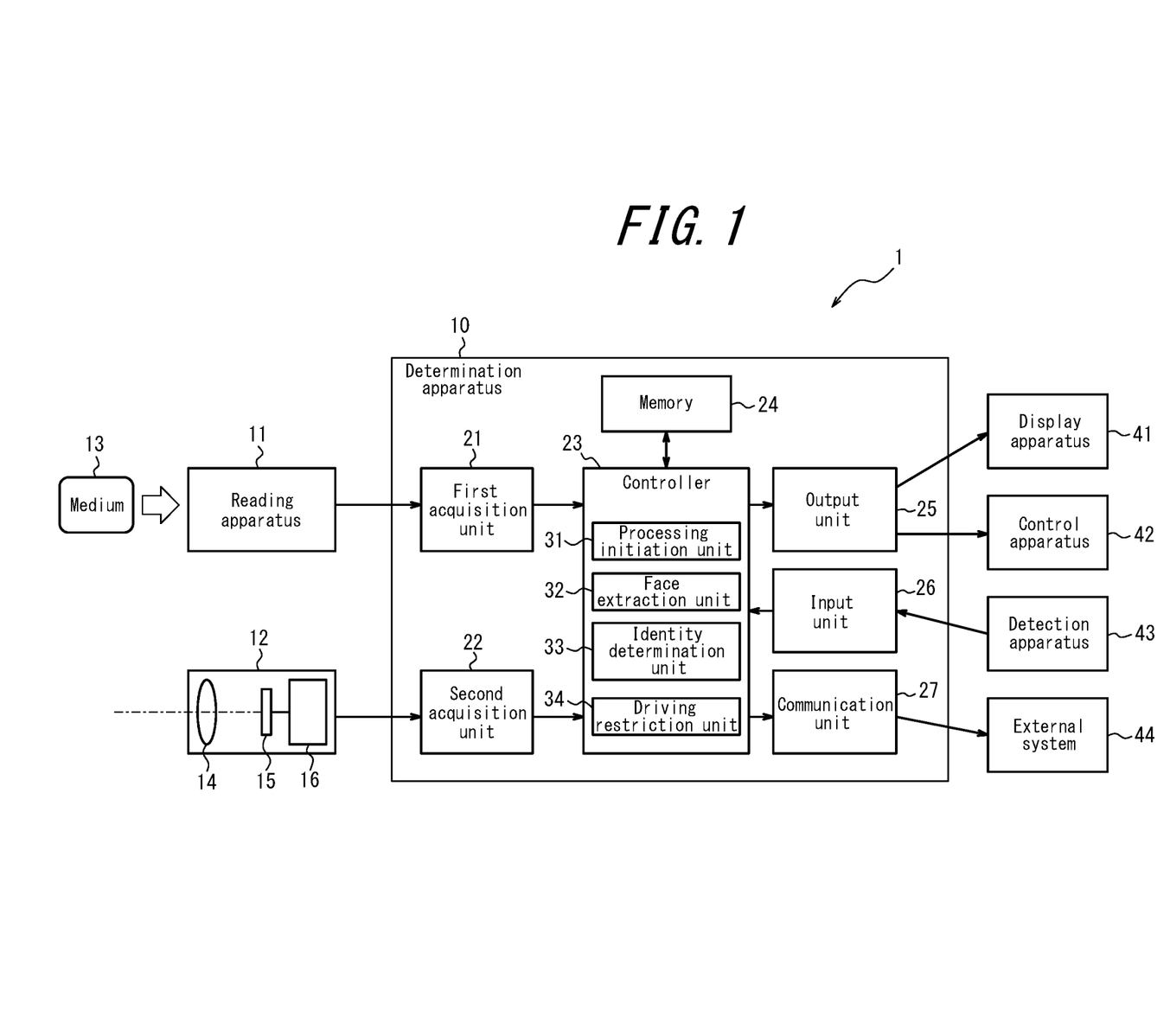
FIG. 1 is a block diagram illustrating the schematic configuration of a driver confirmation system according to an embodiment.

With reference to FIG. 1, the configuration of a driver confirmation system according to an embodiment is described. The driver confirmation system 1 authenticates whether the driver of a particular apparatus is a legitimate driver permitted to drive the apparatus. The particular apparatus may, for example, be a moveable body, a construction machine, an apparatus for operating a factory, a robot controlled by the driver, or the like. Examples of moveable bodies include vehicles, such as automobiles, buses, and trucks; aircraft, helicopters, airships, marine vessels, submarines, personal watercraft, snowmobiles, and the like. The driver confirmation system 1 includes a determination apparatus 10, a reading apparatus 11, and a camera 12.

The reading apparatus 11 reads a facial photograph image as a first facial image from a medium 13 that holds the facial photograph image. The medium 13 is a license, a permit, a certification, a qualification certificate, a membership card, an ID card, an electronic key with an internal memory, or the like that indicates permission for a particular individual to drive a particular apparatus. The medium 13 may be an individual identification medium for identifying an individual or an individual authentication medium for authenticating an individual. The medium 13 may include a memory and hold the facial photograph image in the memory as electronic data. The medium 13 may hold the facial photograph image as a photograph displayed on the surface of the medium 13. The medium 13 may both display the facial photograph image on the surface of the medium 13 and store the facial photograph image in a memory. The medium 13 may have any of various shapes: a card shape, a prismatic shape, a cylindrical shape, a disk shape, or the like.

The reading apparatus 11 may, for example, be a reading apparatus that reads, as electronic data, the facial photograph image stored in the memory of the medium 13. The reading apparatus 11 may include an input unit when authentication by a PIN, a password, or the like is necessary when reading the facial photograph image stored in the memory of the medium 13. The input unit may, for example, be a keyboard, a touch panel, or the like for input of the PIN or password. The reading apparatus 11 may also include a scanner that optically reads the content displayed on the surface of the medium 13, including the facial photograph image. The reading apparatus 11 may extract the facial photograph image from the optically read image and convert the facial photograph image to electronic data.

The camera 12 can capture an image of an imaging area, in which the face of the driver of the apparatus to be driven is assumed to be located, at the start of driving and/or during driving. The imaging area in which the face of the driver is assumed to be located is a wider area than the face of a standard driver. The imaging area in which the face of the driver is assumed to be located can be set to include the position of the face when a driver of average build operates the apparatus to be driven while adopting standard posture. The "start of driving" in the present disclosure refers to when the apparatus to be driven is activated and/or operated in preparation for activation. "Preparation for activation" may, for example, include any of adjusting the seat position, adjusting the steering position, adjusting the mirror angle, operating a brake pedal, and operating a clutch pedal. "During driving" refers to when the apparatus is being driven continuously.

The camera 12 can include an optical system 14 including a lens and the like, an image sensor 15, and a signal processing circuit 16. The optical system 14 forms an image of a subject located in the imaging area on an imaging surface of the image sensor 15. The optical system 14 may include one or more lenses. The image sensor 15 may, for example, be a charge-coupled device (CCD) image sensor or a complementary MOS (CMOS) image sensor. The signal processing circuit 16 generates an image signal representing the image formed by the image sensor 15. The signal processing circuit 16 may perform any process on the image, such as distortion correction, brightness adjustment, contrast adjustment, and/or gamma correction.

The determination apparatus 10 acquires the first facial image from the reading apparatus 11. The determination apparatus 10 extracts, from the captured image acquired from the camera 12, an image of the face of the driver as a second facial image. The determination apparatus 10 compares the first facial image and the second facial image and determines whether the driver is the person in the facial photograph image held by the medium 13. The determination apparatus 10 includes a first acquisition unit 21, a second acquisition unit 22, and a controller 23. The determination apparatus 10 can include one or more of a memory 24, an output unit 25, an input unit 26, and a communication unit 27 as necessary. The memory 24, output unit 25, input unit 26, and communication unit 27 are not, however, essential components. The functions of the determination apparatus 10 are controlled by the controller 23. Operations of the determination apparatus 10 may be synonymous with operations of the controller 23.

The first acquisition unit 21 acquires the facial photograph image included in the medium 13 from the reading apparatus 11. The second acquisition unit 22 receives an image signal from the camera 12 and acquires a captured image that includes the face of the driver and was captured at the start of driving and/or during driving of the apparatus to be driven. The first acquisition unit 21 can be embodied as an input interface corresponding to the transmission format of signals output by the reading apparatus 11, and the second acquisition unit 22 can be embodied as an input interface corresponding to the transmission format of signals output by the camera 12.

The controller 23 controls the determination apparatus 10 overall. The controller 23 includes one or more processors. The controller 23 or the processor may include one or more memories that store programs for various processing and store information during calculations. The term "memory" encompasses volatile memory and non-volatile memory. The memory may be configured as a memory independent from the processor and/or a memory built into the processor. The term "processor" encompasses universal processors that execute particular functions by reading particular programs and dedicated processors that are specialized for particular processing. Dedicated processors include application specific integrated circuits (ASICs) for specific applications. Processors also include programmable logic devices (PLDs). PLDs include field-programmable gate arrays (FPGAs). The controller 23 may be either a system-on-a-chip (SoC) or a system in a package (SiP) with one processor or a plurality of processors that work together.

The controller 23 may include the following functional blocks: a processing initiation unit 31, a face extraction unit 32, an identity determination unit 33, and a driving restriction unit 34. Each functional block may be a hardware module or a software module. The controller 23 can execute the operations performable by each functional block. The controller 23 may execute all of the operations of the functional blocks. The operations performed by each functional block may be synonymous with operations performed by the controller 23. The controller 23 itself may execute the processing that the controller 23 causes any of the functional blocks to perform.

The processing initiation unit 31 initiates determination processing to determine whether the driver photographed by the camera 12 is the person in the facial photograph image held by the medium 13. The processing initiation unit 31 initiates the determination processing before the driver starts driving the apparatus to be driven. The processing initiation unit 31 can initiate the determination processing on the basis of the signal from the reading apparatus 11 acquired by the first acquisition unit 21 and/or a signal from a detection apparatus 43 acquired by the input unit 26. For example, the processing initiation unit 31 may initiate the determination processing when the reading apparatus 11 newly acquires a facial photograph image held by the medium 13. When the apparatus to be driven is a vehicle, the processing initiation unit 31 may initiate the determination processing when the key of the vehicle is inserted in an insertion slot. The processing initiation unit 31 may initiate the determination processing when, for example, a possible switch in drivers during driving of the apparatus to be driven is detected from the detection apparatus 43 via the input unit 26.

The face extraction unit 32 acquires a captured image captured by the camera 12 from the second acquisition unit 22 and extracts an image of the face of the driver as a second facial image. The face extraction unit 32 can use a variety of algorithms for face extraction. For example, an image of a face can be extracted by detecting facial components, such as the eyes, nose, and mouth, from the captured image. An image of a face can also be detected on the basis of the silhouette of body parts such as the head, neck, and shoulders.

The identity determination unit 33 compares the first facial image, which is the facial photograph image included in the medium 13 and acquired from the first acquisition unit 21, and the second facial image extracted from the captured image acquired from the second acquisition unit 22. By this comparison, the identity determination unit 33 determines whether the driver is the person in the facial photograph image held by the medium 13. The determination can be made using various methods. For example, the identity determination unit 33 can calculate feature values related to the arrangement of the eyes, nose, and/or mouth from the images of the faces included in the first facial image and the second facial image and compare the feature values to determine whether they belong to the same person.

When it is not determined that the driver is the person in the facial photograph image held by the medium 13, the driving restriction unit 34 can restrict driving of the apparatus. The driving restriction unit 34 outputs a signal, through the output unit 25, to a control apparatus 42 of the apparatus to be driven so as to restrict driving of the apparatus. In the present disclosure, to "restrict" driving of the apparatus refers to limiting receipt of operations for driving, limiting uses of functions for driving, limiting performance when driving, and the like. The performance includes, for example, the maximum speed at which the apparatus can be driven. The driving restriction unit 34 can also output a signal, through the output unit 25, to the control apparatus 42 of the apparatus to be driven so as to suspend driving. In the present disclosure, to "suspend" driving refers to making driving impossible. In the present disclosure, "restrict" encompasses "suspend". The driving restriction unit 34 may also display a warning on a display apparatus 41 through the output unit 25.

The memory 24 can store the first facial image acquired from the first acquisition unit 21. The first facial image is stored for comparison with the second facial image extracted from the captured image acquired from the second acquisition unit 22. The memory 24 may, for example, include a semiconductor memory, a magnetic memory, an optical memory, or the like. The semiconductor memory may include volatile memory and non-volatile memory. When a memory built into the controller 23 is used to store the first facial image, the memory 24 need not be provided in the determination apparatus 10. The memory 24 may store information other than the first facial image. For example, when the apparatus to be driven is a vehicle used for car sharing, the memory 24 may store identification information such as the name and address of the user of the vehicle.

The output unit 25 is an interface for output to the display apparatus 41, the control apparatus 42, or the like provided in the apparatus to be driven. A physical connector or a wireless communication device can be used in the output unit 25. In an embodiment, the output unit 25 may be connected to a vehicle network, such as a control area network (CAN), when the apparatus to be driven is a vehicle. The determination apparatus 10 may be connected to the control apparatus 42 through the CAN.

When it cannot be determined that the driver is the person in the facial photograph image held by the medium 13, the controller 23 can instruct the control apparatus 42 through the output unit 25 to restrict driving operations by the driver.

When the apparatus to be driven is a vehicle, restriction of driving operations includes suspension of driving operations. Suspension of driving operations may encompass disabling performance of a target operation, disabling a process for receiving a target operation, and disabling a process for operation execution after receipt of a target operation. Driving operations can be suspended by one or more methods such as not starting the engine, disabling operation of the shift knob, and disabling release of the parking brake. When the apparatus to be driven is a vehicle, not starting the engine encompasses disabling rotation of the ignition key to the start position and not starting the engine in conjunction with the immobilizer. Disabling operation of the shift knob encompasses not allowing the shift knob to move from the parking position, not outputting an operation signal of the shift knob when operation of the shift knob is received, and not shifting gears after operation of the shift knob is received. Disabling release of the parking brake encompasses fixing the operation lever of the parking brake to prevent release, deactivating or suspending activation of a parking brake release device, and not outputting a parking brake release signal after a parking brake release operation is received.

Restriction of driving operations is not limited to suspension of the aforementioned driving operations. For example, after starting the engine, the control apparatus 42 can restrict driving operations by not increasing the engine speed above a predetermined speed even when the accelerator is depressed. The control apparatus 42 can also restrict driving operations by disabling operation of an electric mirror.

Driving operations are restricted by cooperation between the controller 23 and the control apparatus 42. Therefore, the present disclosure is not limited to the case of the controller 23 instructing the control apparatus 42 to restrict driving operations by the driver. In an embodiment, the control apparatus 42 may transition to a state capable of restricting driving operations when receiving, from the controller 23, a signal indicating that it cannot be determined that the driver is the person in the facial photograph image held by the medium 13.

When it cannot be determined that the driver is the person in the facial photograph image held by the medium 13, the controller 23 can also display a warning on the display apparatus 41 through the output unit 25. Specifically, the controller 23 can display a warning on the display apparatus 41 indicating that driving is not permitted, such as "Authentication error. You cannot drive". A variety of displays may be used as the display apparatus 41, such as a liquid crystal display (LCD), an organic electro-luminescence (EL) display, an inorganic EL display, or a plasma display panel (PDP).

The input unit 26 is an interface for receiving input from various detection apparatuses 43 provided in the apparatus to be driven. A physical connector or a wireless communication device can be used in the input unit 26. Physical connectors include an electrical connector corresponding to transmission by an electric signal, an optical connector corresponding to transmission by an optical signal, and an electromagnetic connector corresponding to transmission by an electromagnetic wave. Electrical connectors include connectors conforming to IEC 60603, connectors conforming to the USB standard, connectors comprising RCA terminals, connectors comprising S terminals prescribed by EIAJ CP-1211A, connectors comprising D terminals prescribed by EIAJ RC-5237, connectors conforming to the HDMI® standard (HDMI is a registered trademark in Japan, other countries, or both), and connectors comprising a coaxial cable including a BNC connector. Optical connectors include a variety of connectors conforming to IEC 61754. Wireless communication devices include wireless communication devices conforming to standards that include Bluetooth® (Bluetooth is a registered trademark in Japan, other countries, or both) and IEEE802.11. The wireless communication device includes at least one antenna. When the apparatus to be driven is a vehicle, the input unit 26 may connect to a vehicle network such as a CAN. In an embodiment, the input unit 26 is a separate constituent element from the first acquisition unit 21 and the second acquisition unit 22, but this configuration is not limiting. In an embodiment, the first acquisition unit 21, the second acquisition unit 22, and the input unit 26 may be implemented as one input unit. At least a portion of the first acquisition unit 21, the second acquisition unit 22, and the input unit 26 may be implemented along with the output unit 25 as one input/output unit.

The input unit 26 transmits the output of the detection apparatus 43 to the controller 23. When the apparatus to be driven is a vehicle, the detection apparatus 43 may, for example, be a sensor for detecting operation of the ignition key, operation of the parking brake, operation of the shift knob, or the like. The processing initiation unit 31 of the controller 23 may execute the above-described determination processing when the driver performs at least one of these operations at the start of driving.

When the apparatus to be driven is a vehicle, the detection apparatus 43 may, for example, be a sensor for detecting that the driver is sitting in the driver's seat or a sensor for detecting attachment or detachment of the seatbelt. The detection apparatus 43 may also function as the camera 12. In this case, the camera 12 may monitor the presence of the driver's head in the imaging area and output a signal when the head is not detected. The processing initiation unit 31 of the controller 23 may start the determination processing when the detection apparatus 43 detects a predetermined event. Detection of a predetermined event includes the case of the detection apparatus 43 detecting attachment or detachment of the driver's seat seatbelt, the case of the driver not being detected in images captured by the camera 12 for a predetermined time or longer, and the case of the detection apparatus 43 being a vehicle seat sensor and not detecting sitting by the driver for a predetermined time or longer.

The communication unit 27 is an interface for communicating with a destination external to the apparatus to be driven. When it cannot be determined that the driver is the person in the facial photograph image held by the medium 13, the controller 23 can notify an external system 44 through the communication unit 27. When the apparatus to be driven is a vehicle, the external system 44 can, for example, be a system of a security company or a rental car company. When it cannot be determined that the driver photographed by the camera 12 is the person in the facial photograph image held by the medium 13, the controller 23 notifies the external system 44 that someone other than the legitimate user is attempting to drive the vehicle. In this case, the controller 23 may also transmit the captured image of the driver's face photographed by the camera 12 to the external system 44.

The driver confirmation system 1 according to an embodiment can be mounted in a moveable body, in particular a vehicle, that can be operated by a driver. The term "vehicle" in the present disclosure includes, but is not limited to, automobiles, railway vehicles, industrial vehicles, and vehicles for daily life. For example, the term "vehicle" may include airplanes that travel down a runway. Automobiles include, but are not limited to, passenger vehicles, trucks, buses, motorcycles, and trolley buses, and may include other vehicles that travel on the road. Railway vehicles include, but are not limited to, locomotives, streetcars, guided railway vehicles, linear motor cars, and monorails, and may include other vehicles that travel along a track. Industrial vehicles include industrial vehicles for agriculture and for construction. Industrial vehicles include, but are not limited to, forklifts and golf carts. Industrial vehicles for agriculture include, but are not limited to, tractors, cultivators, transplanters, binders, combines, and lawnmowers. Industrial vehicles for construction include, but are not limited to, bulldozers, scrapers, backhoes, cranes, dump cars, and road rollers. Vehicles for daily life include, but are not limited to, bicycles and motorized, two-wheeled standing vehicles. Power engines for the vehicle include, but are not limited to, internal-combustion engines including diesel engines, gasoline engines, and hydrogen engines, and electrical engines including motors. The vehicle is not limited to the above-listed types. For example, automobiles may include industrial vehicles that can drive on the road, and the same vehicle may be included in multiple categories.

Figure 2:
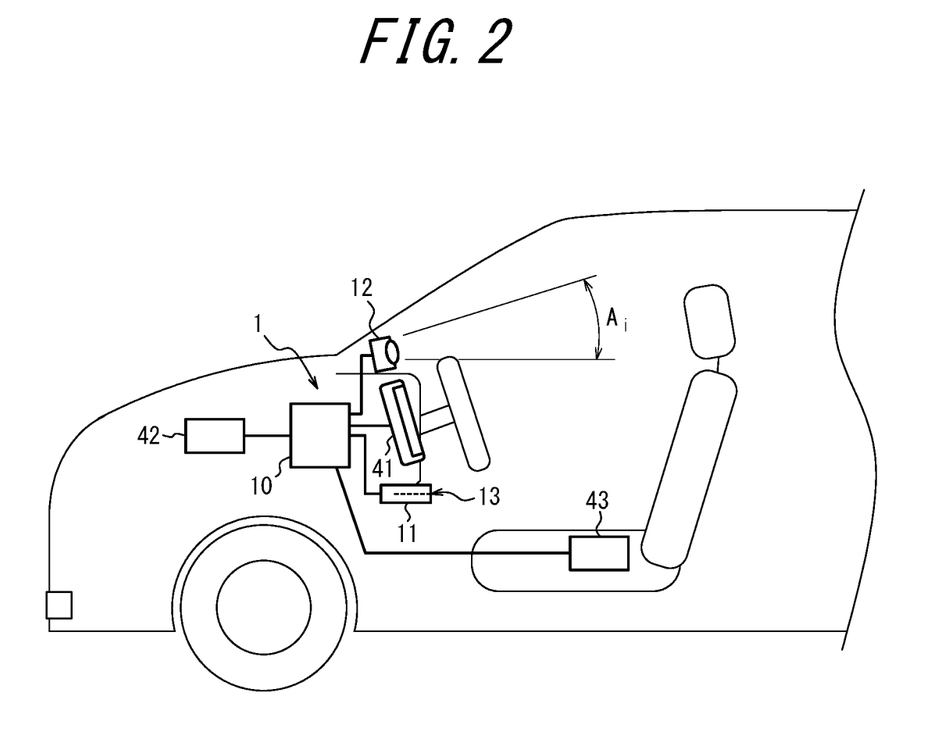
FIG. 2 illustrates an example arrangement of constituent elements when the driver confirmation system of FIG. 1 is mounted in a vehicle.

With reference to FIG. 2, the configuration of a driver confirmation system 1 mounted in a vehicle according to an embodiment is described. FIG. 2 illustrates a portion of the constituent elements in FIG. 1. However, the constituent elements that are illustrated in FIG. 1 but not in FIG. 2 can also be mounted in the vehicle. Each constituent element in FIG. 1 can also be mounted in the driver confirmation system 1 that is mounted in the vehicle.

In FIG. 2, the determination apparatus 10 is disposed inside the dashboard of the vehicle. The determination apparatus 10 is not limited to being disposed at this position and may be disposed at another location in the vehicle. The reading apparatus 11 can be installed inside or on top of the dashboard. Alternatively, the reading apparatus 11 can be disposed at any other position inside the vehicle cabin near the driver's seat.

A driver's license can be used as an example of the medium 13 used in the driver confirmation system 1 mounted in the vehicle. A facial photograph image of the license holder is displayed on the driver's license. A contactless integrated circuit (IC) chip is embedded in Japanese driver's licenses. Electronic data of the facial photograph image, and of information such as the license holder's name and the type of license, is recorded on this IC chip. This electronic data can be read by using a reading apparatus 11 compatible with driver's licenses. Apart from contactless media, contact media such as a contact IC card can also be used as the medium 13 that holds electronic data.

Figure 3:
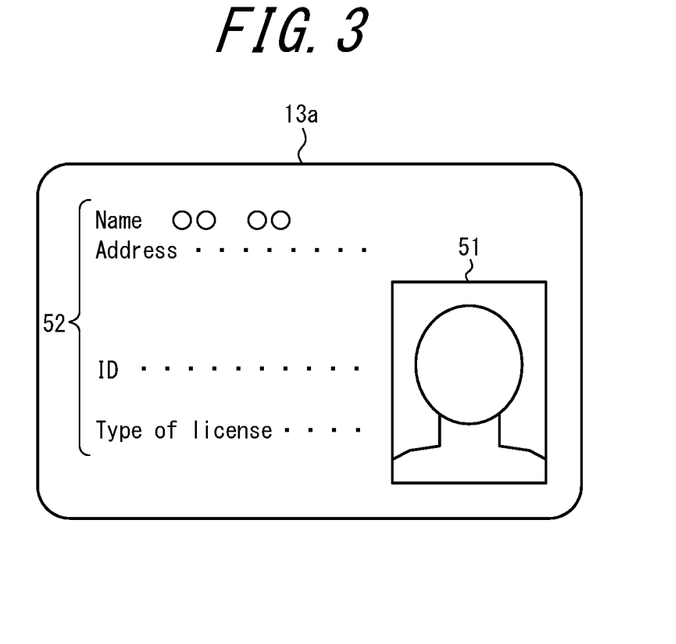
FIG. 3 illustrates an example medium on which a facial photograph is displayed.

FIG. 3 illustrates an example of a medium 13a assumed to be the surface of a driver's license. A facial photograph 51 and driver information 52 are displayed on the surface of the medium 13. The driver information 52 is information such as the name and address of the driver and the type of driver's license. The reading apparatus 11 may optically scan the facial photograph 51 on the medium 13 to acquire the facial photograph image. Along with the facial photograph image, the reading apparatus 11 may also acquire the driver information 52 using optical character recognition.

Figure 4:
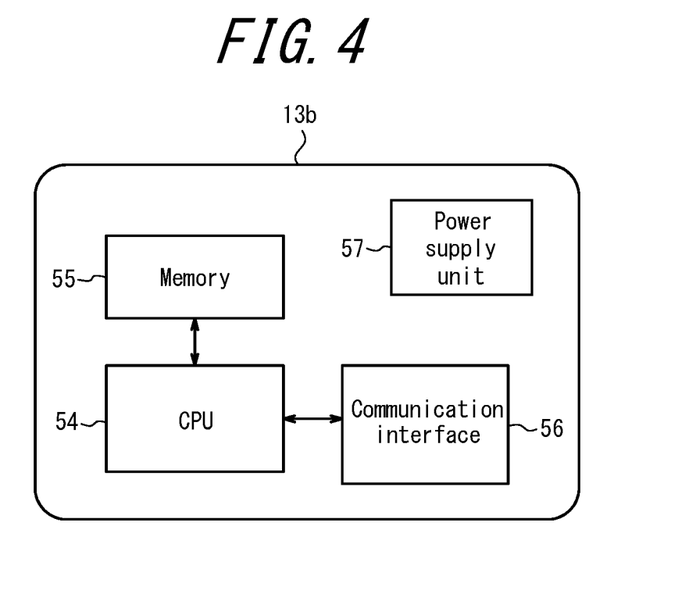
FIG. 4 is a block diagram illustrating an example configuration of the medium.

FIG. 4 illustrates an example of a medium 13b assumed to be a driver's license in which a contactless IC chip is embedded. The medium 13b includes a central processing unit (CPU) 54, a memory 55, a communication interface 56, and a power supply unit 57. The IC chip includes the CPU 54 and the memory 55. The memory 55 stores electronic data of the facial photograph image along with the driver information 52, such as the name of the license holder and the type of license. The CPU 54 can receive a request to read electronic data from the reading apparatus 11 through the communication interface 56 and transmit the electronic data. The communication interface 56 includes an antenna coil connected to the IC chip and can communicate with the reading apparatus 11 by methods such as electromagnetic induction. In this case, the reading apparatus 11 can be a reader/writer of a contactless IC card. The power supply unit 57 may receive electromagnetic waves, transmitted by the reading apparatus 11, through the antenna of the communication interface 56, convert the electromagnetic waves to electric power, and supply the electric power to the CPU 54 and memory 55. The power supply unit 57 may also have a built-in battery to supply electric power to the CPU 54 and the memory 55.

The driver information 52 acquired from the medium 13a and/or 13b may be transmitted to the determination apparatus 10 and used by the controller 23. For example, the controller 23 can determine whether the type of driver's license conforms to the vehicle to be driven. When determining that the type of driver's license does not conform, the controller 23 may suspend driving even when determining that the driver is the same as the person in the facial photograph image held by the medium 13. In a vehicle for car sharing, the controller 23 may suspend driving when the name and address do not match member information registered in the memory 24.

In FIG. 2, the camera 12 can be disposed on the dashboard of the vehicle. The camera 12 is not limited to being installed at this position and may be located at any position allowing imaging of an imaging area Ai in which the face of the seated driver is assumed to be located. The camera 12 may, for example, be installed in a meter hood, on top of the steering column, or at the upper portion of the windshield. The camera 12 can also function as a camera for monitoring the state of the driver to prevent the driver from falling asleep at the wheel.

The display apparatus 41 can be attached at any position visible to the driver, such as in or on the dashboard. A liquid crystal display for a car navigation system mounted in the vehicle can, for example, be used as the display apparatus 41. A dedicated display for the driver confirmation system 1 may also be provided as the display apparatus 41.

The control apparatus 42 can be a control device or an electronic control unit that controls the different parts of the vehicle. When the determination apparatus 10 determines that the driver is not the person in the facial photograph image held by the medium 13, the determination apparatus 10 transmits a signal to various control apparatuses 42 to restrict or suspend driving operations. The various control apparatuses 42 may include any of an engine start control device that enables starting of the engine, an accelerator control device that enables the accelerator, a shifting control device that enables movement of the shift knob, a parking brake control device that enables movement of the parking brake, and the like.

The example detection apparatus 43 illustrated in FIG. 2 is a seat sensor for detecting that the driver is sitting in the seat. The seat sensor can be a pressure sensor provided inside the driver's seat. When the seat sensor does not detect sitting by the driver for a predetermined time or longer and subsequently detects sitting by the driver, the driver may have switched. Hence, even during driving, the determination apparatus 10 initiates the determination processing for determining whether the driver is the person in the facial photograph image held by the medium 13. The driver may switch in this way during driving when the vehicle is driving autonomously.

The detection apparatus 43 can use a variety of sensors provided in the vehicle other than the seat sensor to detect the possible switch in drivers. For example, a pressure sensor for detecting that a foot has been placed on a foot rest, a sensor for detecting that the driver is gripping the steering wheel, or the like may be included as the detection apparatus 43. A grip sensor for detecting pressure on the steering wheel, for example, can be used to recognize whether the driver is gripping the steering wheel. It can also be recognized whether the driver is gripping the steering wheel by detecting counter torque acting on the steering wheel. As described above, the camera 12 can function as the detection apparatus 43.

Figure 5:
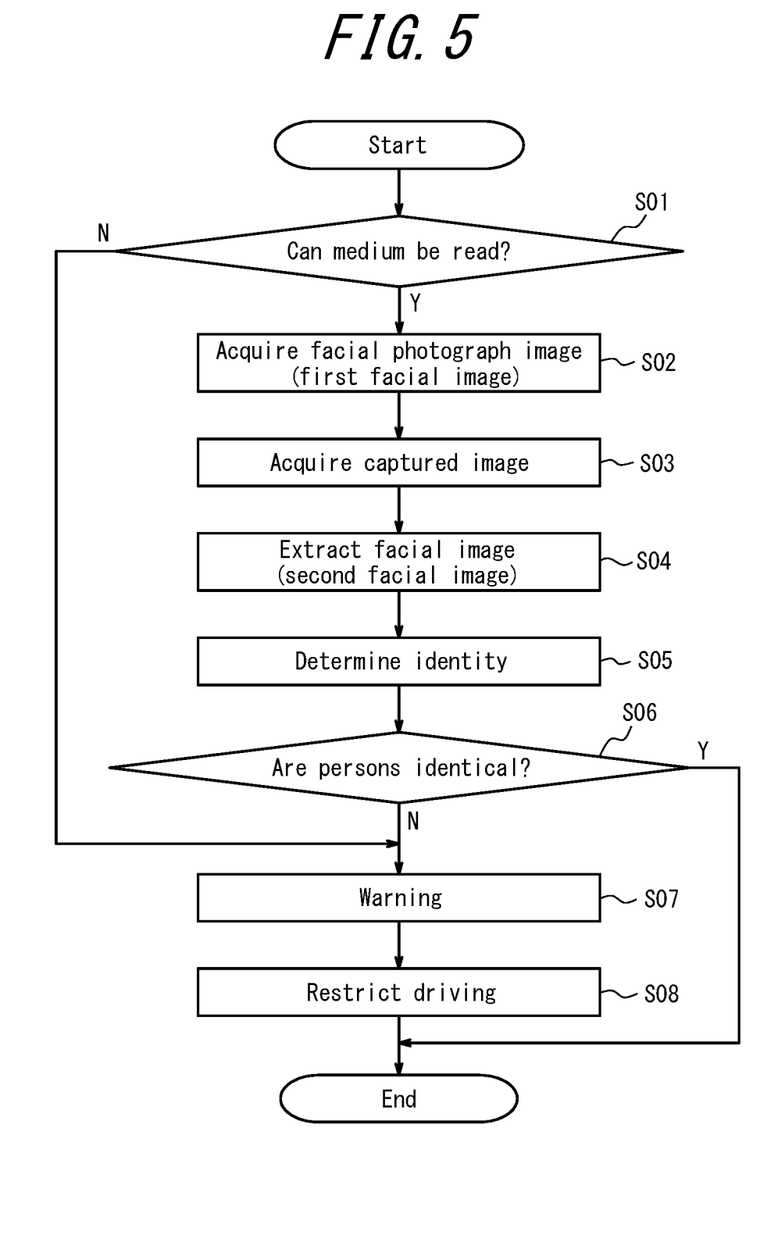
FIG. 5 is a flowchart illustrating example processing by a controller in the driver confirmation system of FIG. 1.

Next, the detection processing executed by the controller 23 is described with reference to FIG. 5.

In response to the various conditions described above, the processing initiation unit 31 of the controller 23 initiates the determination processing. When the determination processing is initiated by the processing initiation unit 31, the controller 23 judges whether the reading apparatus 11 can read the facial photograph image of the medium 13 (step S01). The controller 23 can make this judgment on the basis of whether the facial photograph image can be acquired from the first acquisition unit 21. When the facial photograph image cannot be acquired, it may be that the medium 13 is not inserted readably in the reading apparatus 11. In this case, the controller 23 proceeds to the processing from step S07 on, described below. When the facial photograph image can be acquired from the first acquisition unit 21, the controller 23 acquires and stores the facial photograph image as a first facial image in the memory 24 (step S02).

The controller 23 acquires a captured image captured by the camera 12 from the second acquisition unit 22 (step S03).

Next, the controller 23 uses the face extraction unit 32 to extract an image of a face as a second facial image from the captured image acquired in step S03 (step S04).

The controller 23 uses the identity determination unit 33 to determine whether the first facial image acquired in step S02 and the second facial image extracted in step S04 are the same (step S05).

The processing by the controller 23 branches on the basis of the result of the determination of identity (step S06). When it is determined that the person in the first facial image and the person in the second facial image are the same, the controller 23 ends the processing without restricting driving in any way. Before ending the processing, the controller 23 may store the facial photograph 51 and driver information 52 of the current driver and/or information such as the time of determination in the memory 24. When the controller 23 cannot judge that the person in the first facial image and the person in the second facial image are the same, the processing proceeds to step S07.

In step S07, the controller 23 issues a warning via the output unit 25. This warning includes displaying a warning that the driver is not a legitimate driver on the display apparatus 41. The controller 23 may cause a speaker inside the vehicle to emit a warning sound.

Furthermore, the controller 23 transmits a signal to the control apparatus 42 through the output unit 25 for the control apparatus 42 to restrict driving by the driver (step S08). The method by which the control apparatus 42 restricts driving may differ in accordance with the conditions when the driver confirmation system 1 confirms the driver by the determination processing. For example, when the driver is confirmed at the start of driving, the control apparatus 42 can disable engine activation and/or shift knob operation or the like to suspend the start of driving. When the driver is confirmed during driving, the controller 23 may first issue a warning to the driver. In conjunction with the control apparatus 42, the controller 23 may then slow the vehicle down, move the vehicle to the shoulder of the road being driven on, and stop the vehicle. Alternatively, before restricting driving, the controller 23 may prompt the driver to insert a proper medium 13, i.e. license, in the reading apparatus 11 in step S07.

As described above, the driver confirmation system 1 of the present embodiment compares a first facial image included in the medium 13, which holds a facial photograph image, and a second facial image of the driver obtained by capturing an image of the driver at the start of driving and/or during driving and determines whether the facial images are of the same person. In this way, driving can be limited to legitimate drivers only. When the medium 13 is a driver's license, driving by a non-legitimate driver that does not possess a driver's license can be deterred. At this time, the driver need not perform any cumbersome operations such as registering a facial photograph image of the driver or the like in advance.

The driver confirmation system 1 according to the present embodiment can judge whether the person in the facial photograph image of the medium 13 and the driver included in the captured image are the same not only at the start of driving but also during driving. It can therefore be detected that the driver has switched during driving of the apparatus to be driven. A warning can then be issued, and driving can be restricted or suspended.

Figure 6:
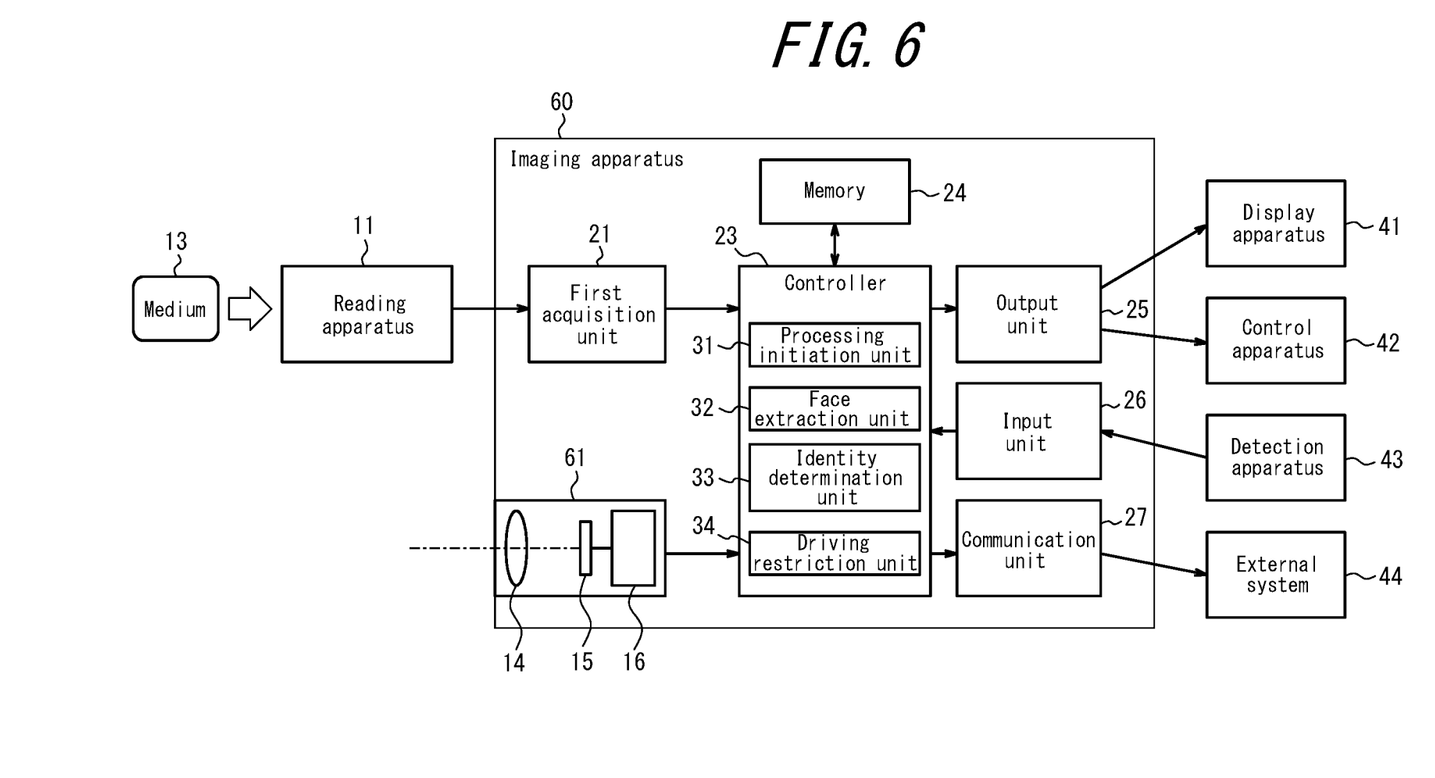
FIG. 6 is a block diagram illustrating the schematic configuration of an imaging apparatus according to an embodiment.

FIG. 6 illustrates an imaging apparatus 60 according to an embodiment along with the above-described reading apparatus 11, display apparatus 41, control apparatus 42, detection apparatus 43, and external system 44. Constituent elements that are identical or correspond to the constituent elements in FIG. 1 and constituent elements that have identical or corresponding operations are labeled with the same reference signs, and a description thereof is omitted. In the embodiment in FIG. 6, the controller 23 controls the imaging apparatus 60 overall.

Along with an imaging unit 61 provided with the optical system 14, the image sensor 15, and the signal processing circuit 16, the imaging apparatus 60 includes all of the constituent elements of the determination apparatus 10 in FIG. 1. In this way, the imaging apparatus 60 extracts the second facial image from the captured image of the driver. Furthermore, the imaging apparatus 60 can compare the second facial image with the first facial image held by the medium 13 and acquired from the reading apparatus 11 to determine whether the driver is a legitimate driver. Accordingly, the imaging apparatus 60 can obtain the same effects as the driver confirmation system 1.

The present disclosure is not limited to the above embodiments, and a variety of modifications and changes are possible. For example, the functions and the like included in the various components and steps may be reordered in any logically consistent way. Components, steps, or the like may also be combined into one or divided. For example, the reading apparatus and/or display apparatus may be provided in the same housing as the determination apparatus or the imaging apparatus. While embodiments of the present disclosure have been described focusing on apparatuses, the present disclosure may also be embodied as a method that includes steps performed by the components of an apparatus.

When the facial photograph image is displayed on the surface of the medium in the above embodiment, the reading apparatus has been described as optically reading the content displayed on the surface of the medium, including the facial photograph image, and extracting the facial photograph image from the read image. The determination apparatus, however, may extract the facial photograph image instead of the reading apparatus. In this case, the facial photograph image acquired by the first acquisition unit may be considered an image that includes a facial photograph and other content.

Use of the present disclosure is not limited to suspending driving by a non-legitimate driver. For example, when a plurality of drivers take turns driving a vehicle such as a long-distance bus, the driving time by the same driver can be measured, and a warning can be issued when a predetermined time is exceeded. At this time, the driver's license photograph and the image of the driver's face captured by the camera are compared, making it possible to determine whether the driver who possesses the driver's license and the actual driver are the same.

REFERENCE SIGNS LIST

1 Driver confirmation system
10 Determination apparatus
11 Reading apparatus
12 Camera
13, 13a, 13b Medium
14 Optical system
15 Image sensor
16 Signal processing circuit 21 First acquisition unit
22 Second acquisition unit
23 Controller
24 Memory
25 Output unit
26 Input unit
27 Communication unit
31 Processing initiation unit
32 Face extraction unit
33 Identity determination unit
34 Driving restriction unit
41 Display apparatus
42 Control apparatus
43 Detection apparatus
44 External system
51 Facial photograph
52 Driver information
54 CPU
55 Memory
56 Communication interface
57 Power supply unit
60 Imaging apparatus
61 Imaging unit
Ai Imaging area

The invention claimed is:

1. A determination apparatus comprising:
a processor configured to,
  acquire a facial photograph image, included in a medium holding the facial photograph image, as a first facial image,
  acquire a captured image obtained by capturing an image of an imaging area, in which a face of a driver is located, at a start of driving and/or during driving a moveable body,
  extract an image of the face of the driver as a second facial image from the captured image,
  compare the first facial image and the second facial image,
  determine whether the driver is a person in the facial photograph image held by the medium, and
  determine whether the driver is permitted to drive the moveable body based on one or both of,
    whether the medium indicates a type of driver's license that matches a type of the moveable body, or
    whether the medium indicates an identifier of the driver that matches member information for the moveable body.

2. The determination apparatus of claim 1, wherein the processor is configured to acquire the facial photograph image as electronic data.

3. The determination apparatus of claim 1, wherein the facial photograph image is optically read from the surface of the medium.

4. An imaging apparatus comprising:
a processor configured to,
  capture an image of an imaging area, in which a face of a driver is located, at a start of driving and/or during driving a moveable body,
  acquire a facial photograph image, included in a medium holding the facial photograph image, as a first facial image,
  extract an image of the face of the driver as a second facial image from the captured image,
  compare the first facial image and the second facial image,
  determine whether the driver is a person in the acquired facial photograph image, and
  determine whether the driver is permitted to drive the moveable body based on one or both of,
    whether the medium indicates a type of driver's license that matches a type of the moveable body, or
    whether the medium indicates an identifier of the driver that matches member information for the moveable body.

5. A driver confirmation system comprising:
a camera configured to capture an image of an imaging area, in which a face of a driver is located, at a start of driving and/or during driving a moveable body; and
a processor configured to,
  read a facial photograph image as a first facial image from a medium holding the facial photograph image,
  extract an image of the face of the driver as a second facial image from a captured image acquired from the camera,
  compare the first facial image and the second facial image,
  determine whether the driver is a person in the facial photograph image, and
  determine whether the driver is permitted to drive the moveable body based on one or both of,
    whether the medium indicates a type of driver's license that matches a type of the moveable body, or
    whether the medium indicates an identifier of the driver that matches member information for the moveable body.

6. The driver confirmation system of claim 5, further comprising:
an output device;
wherein the processor is configured to issue a warning to the driver through the output device when it cannot be determined that the driver is the person in the facial photograph image.

7. The driver confirmation system of claim 5, further comprising:
a communication device;
wherein the processor is configured to notify an external destination through the communication device when it cannot be determined that the driver is the person in the facial photograph image held by the medium.

8. A moveable body comprising:
a driver confirmation system, the driver confirmation system comprising:
  a camera configured to capture an image of an imaging area, in which a face of a driver is assumed to be located, at a start of driving and/or during driving; and
  a processor configured to,
    read a facial photograph image as a first facial image from a medium holding the facial photograph image,
    extract an image of the face of the driver as a second facial image from a captured image acquired from the camera,
    compare the first facial image and the second facial image,
    determine whether the driver is a person in the facial photograph image, and
    determine whether the driver is permitted to drive the moveable body based on one or both of, whether the medium indicates a type of driver's license that matches a type of the moveable body, or whether the medium indicates an identifier of the driver that matches member information for the moveable body.

9. The moveable body of claim 8, wherein the processor is further configured to restrict a driving operation by the driver when it cannot be determined that the driver is the person in the facial photograph image.

10. The moveable body of claim 9, wherein the moveable body is a vehicle, and the driving operation is restricted by one or more of the following: not starting an engine, disabling operation of a shift knob, and disabling release of a parking brake.

11. The moveable body of claim 8, further comprising an output device, wherein the processor is configured to issue a warning to the driver through the output device when it cannot be determined that the driver is the person in the facial photograph image.

12. The moveable body of claim 8, further comprising a communication device, wherein the processor is configured to notify a destination external to the moveable body through the communication device when it cannot be determined that the driver is the person in the facial photograph image.

13. The moveable body of claim 12, wherein, the processor is further configured also to transmit the captured image of the face of the driver captured by the camera through the communication device when notifying the destination external to the moveable body.

14. The moveable body of claim 8, wherein the processor is configured to determine whether the driver in the image captured by the camera is the person in the facial photograph image held by the medium when a predetermined condition indicating a possible switch in drivers is satisfied.

15. The moveable body of claim 14, wherein the predetermined condition is selected from among the following: detection of attachment or detachment of a driver's seat seatbelt, a driver not being detected in images captured by the camera for a predetermined time or longer, and a seat sensor of the moveable body not detecting sitting by a driver for a predetermined time or longer.

16. A determination method comprising:
acquiring a facial photograph image as a first facial image from a medium holding the facial photograph image;
acquiring a captured image obtained by capturing an image of an imaging area, in which a face of a driver is assumed to be located, at a start of driving and/or during driving a moveable body;
extracting an image of the face of the driver as a second facial image from the captured image;
comparing the first facial image and the second facial image to determine whether the driver is a person in the facial photograph image held by the medium; and
determining whether the driver is permitted to drive the moveable body based on one or both of,
whether the medium indicates a type of driver's license that matches a type of the moveable body, or
whether the medium indicates an identifier of the driver that matches member information for the moveable body.

* * * * *